(12) United States Patent
Sakagami

(10) Patent No.: US 9,228,945 B2
(45) Date of Patent: Jan. 5, 2016

(54) SENSOR CHIP, DETECTION DEVICE, AND METHOD OF MANUFACTURING SENSOR CHIP

(75) Inventor: Yusuke Sakagami, Shiojiri (JP)

(73) Assignee: Seiko Epson Corporation (JP)

( * ) Notice: Subject to any disclaimer, the term of this patent is extended or adjusted under 35 U.S.C. 154(b) by 230 days.

(21) Appl. No.: 13/334,861

(22) Filed: Dec. 22, 2011

(65) Prior Publication Data

US 2012/0162640 A1 Jun. 28, 2012

(30) Foreign Application Priority Data

Dec. 24, 2010 (JP) .................................. 2010-287189

(51) Int. Cl.
*G01N 21/552* (2014.01)
*G01J 3/44* (2006.01)
*G01N 21/65* (2006.01)
*H01L 27/144* (2006.01)

(52) U.S. Cl.
CPC .................. *G01N 21/554* (2013.01); *G01J 3/44* (2013.01); *G01N 21/658* (2013.01); *H01L 27/1446* (2013.01)

(58) Field of Classification Search
CPC ........ G01J 3/44; G01N 21/554; G01N 21/658
USPC ......................................... 356/300, 301, 244
See application file for complete search history.

(56) References Cited

U.S. PATENT DOCUMENTS

| | | | |
|---|---|---|---|
| 7,787,117 B1 | 8/2010 | Leona et al. | |
| 7,952,705 B2 | 5/2011 | Shen et al. | |
| 8,537,353 B2 * | 9/2013 | Liu et al. | 356/300 |
| 2004/0023293 A1* | 2/2004 | Kreimer et al. | 435/7.1 |
| 2005/0211566 A1 | 9/2005 | Tomita et al. | |
| 2006/0275541 A1 | 12/2006 | Weimer | |
| 2007/0263221 A1 | 11/2007 | Naya et al. | |
| 2008/0003576 A1 | 1/2008 | Zhang et al. | |

(Continued)

FOREIGN PATENT DOCUMENTS

| | | |
|---|---|---|
| EP | 1553400 A1 | 7/2005 |
| EP | 1 580 305 A2 | 9/2005 |

(Continued)

OTHER PUBLICATIONS

Extended European Search Report for Application No. EP 11 19 5171 dated Aug. 21, 2013 (6 pages).

(Continued)

*Primary Examiner* — Gregory J Toatley, Jr.
*Assistant Examiner* — Hina F Ayub
(74) *Attorney, Agent, or Firm* — Harness, Dickey & Pierce, P.L.C.

(57) ABSTRACT

A sensor chip includes a substrate, a relief structure composed of protruding sections formed so as to be arranged on a surface of the substrate to have a lattice shape and a recessed section between the protruding sections, and fine metal particles arranged along upper ridge lines of the respective protruding sections of the relief structure, the protruding sections being adjacent to each other, having a minute gap with which the surface plasmon resonance occurs. By irradiating the gap between the fine metal particles with a laser beam, the localized surface plasmon resonance occurs more efficiently. As a result, the sensor chip capable of taking out the surface enhanced Raman scattering to thereby detect the substance with high sensitivity can be realized.

6 Claims, 12 Drawing Sheets

(56) References Cited

U.S. PATENT DOCUMENTS

| | | | |
|---|---|---|---|
| 2009/0097022 A1 | 4/2009 | Shen et al. | |
| 2009/0242854 A1 | 10/2009 | Li et al. | |
| 2010/0040979 A1 | 2/2010 | Weimer | |
| 2010/0053605 A1* | 3/2010 | Ragucci et al. | 356/301 |
| 2010/0245814 A1 | 9/2010 | Jablonski et al. | |
| 2010/0284001 A1* | 11/2010 | Moskovits et al. | 356/301 |
| 2011/0026019 A1 | 2/2011 | Tyagi et al. | |

FOREIGN PATENT DOCUMENTS

| | | |
|---|---|---|
| JP | 2000-356587 | 12/2000 |
| JP | 2005-195440 A | 7/2005 |

OTHER PUBLICATIONS

T. Bhuvana et al., "Inkjet Printing of Palladium Alkanethiolates for Facile Fabrication of Metal Interconnects and Surface-Enhanced Raman Scattering Substrates", The Institution of Engineering and Technology, Micro & Nano Letters, vol. 5, Iss. 5, pp. 296-299, Oct. 31, 2010.

Lee, Hsien-Hsueh et al., "Inkjet Printing of Nanosized Silver Colloids", Nanotechnology V. 16, Institute of Physics Publishing, Department of Chemical Engineering, National Tsing Hua University, Sep. 2, 2005, pp. 2436-2441.

* cited by examiner

SENSOR CHIP, DETECTION DEVICE, AND METHOD OF MANUFACTURING SENSOR CHIP

BACKGROUND

1. Technical Field

The present invention relates to a sensor chip, a detection device using the sensor chip, and a method of manufacturing the sensor chip.

2. Related Art

Recent years, demand for sensors used for medical diagnostics or inspections of food and drink has increased, and further, development of a sensor and a detection device small in size and capable of performing sensing at high speed has been demanded. In order to meet such demand, a variety of types of sensors such as a sensor using an electrochemical process have been studied. Among these sensors, sensors using surface plasmon resonance (SPR) have been receiving increasing attention on the ground of possibility of integration, low cost, and applicability in all measurement environments.

Due to the background described above, with a goal of improvement in sensor sensitivity, there has been proposed a sensor utilizing localized surface plasmon resonance (LSPR) using fine metal particles or a fine metal particles. For example, there is a sensor for detecting a variation in medium in the vicinity of a fine metal particle to thereby detect adsorption or deposition of a target substance (detection target substance) by irradiating a transparent substrate having the fine metal particles fixed on the surface to form a film with a light and then measuring the absorbance of the light transmitted through the fine metal particles (see, e.g., JP-A-2000-356587 (Document 1)).

In Document 1 mentioned above, it is difficult to manufacture the fine metal particles so as to have a uniform size (dimension and shape), and to regularly arrange the fine metal particles. If the sizes and the arrangement of the fine metal particles fail to be controlled, variations are also caused in absorption and resonant wavelength generated by the surface plasmon resonance. Thus, it results that the width of the absorbance spectrum is broadened, and the peak intensity is decreased. Therefore, the signal variation for detecting the variation in the medium in the vicinity of the fine metal particle is low, and the improvement in the sensor sensitivity is limited.

SUMMARY

An advantage of some aspects of the invention is to solve at least a part of the problem described above, and the invention can be implemented as the following forms pr application examples.

Application Example 1

This application example of the invention is directed to a sensor chip including a substrate, a relief structure formed on a surface of the substrate so as to be arranged to form a lattice shape, and a plurality of fine metal particles supported so as to have contact with upper ridgelines of protruding sections of the relief structure, the protruding sections being adjacent to each other, wherein at least a part of the plurality of fine metal particles has a gap between the fine metal particles adjacent to each other.

This application example of the invention is for measuring the Raman scattering using the surface plasmon resonance occurring by irradiating the fine metal particles having the size in the order of several nanometers with the laser beam. According to this application example of the invention, since it results that the fine metal particles are arranged in accordance with the distance between the protruding sections formed on the substrate surface, the fine metal particles are arranged so that the directions of the minute gaps formed between the fine metal particles are aligned with each other. Therefore, by irradiating the gaps between the fine metal particles with the laser beam, the surface enhanced plasmon resonance is developed, and thus the sensor chip capable of detecting the substance with sensitivity can be realized.

Application Example 2

In the sensor chip according to the above application example of the invention, it is preferable that the gap is a minute gap causing surface plasmon resonance, and the substrate is made of a dielectric material.

Here, as the dielectric material, quartz, quartz crystal, glass such as borosilicate glass, silicon, and so on are suitable. It should be noted that in the case of setting the incident light to the substrate side, the substrate which is transparent with respect to the incident light is suitable, and in the case of setting the incident light to the fine metal particle side, the substrate is not necessarily required to be transparent.

In the above application example of the invention, the minute gap of causing the surface plasmon resonance is formed between the fine metal particles, and it is possible to enhance the Raman scattered light by the enhanced electric field due to the localized surface plasmon resonance occurring in the periphery of the fine metal particles to thereby further improve the detection sensitivity. Further, by using a dielectric material as the material of the substrate, the influence of the medium in the periphery of the fine metal particles on the electric field can be eliminated to thereby prevent the peak intensity of the spectrum from being deteriorated.

Application Example 3

In the sensor chip according to the above application example of the invention, it is preferable that an average particle diameter of the fine metal particles is smaller than a wavelength of an incident light, and has a size with which an enhanced electric field due to the surface plasmon resonance is formed.

In the case of irradiating the fine metal particles smaller than the wavelength of the incident light with the light, it results that the free electrons existing on the surface of each of the fine metal particles are subjected to the action of the electric field of the incident light to thereby resonate. Thus, the condition in which the electric dipoles due to the free electrons are aligned is created in the periphery of each of the fine metal particles, and the enhanced electric field stronger than the electric field of the incident light can be formed.

Application Example 4

In the sensor chip according to the above application example of the invention, it is preferable that the distance between the protruding sections of the relief structure, the protruding sections being adjacent to each other, is smaller than the average particle diameter of the fine metal particles.

According to this configuration, it is possible to arrange the fine metal particles with appropriate gaps due to the upper ridgelines of the protruding sections without dropping off in the recessed sections.

Application Example 5

In the sensor chip according to the above application example of the invention, it is preferable that the fine metal particles are each made of one of gold (Au), silver (Ag), copper (Cu), aluminum (Al), platinum (Pt), palladium (Pd), molybdenum (Mo), and chromium (Cr), and alloys and complexes of any of these metals.

If those made of the material described above are used as the fine metal particles, it is possible to develop the surface plasmon resonance (SPR), the localized surface plasmon resonance (LSPR), and the surface enhanced Raman scattering (SERS), and in particular, Au or Ag can develop these phenomena strongly, and thus it becomes possible to detect the detection target substance with high sensitivity.

Application Example 6

This application example of the invention is directed to a method of manufacturing a sensor chip, including: forming a relief structure arranged on a substrate surface to have a lattice shape, ejecting a dispersion liquid having fine metal particles dispersed in a dispersion medium on an upper part of the relief structure, and removing the dispersion medium.

The relief structure is formed using, for example, a laser interference exposure process and an etching process. Thus, the arrangement of the relief pattern can be formed as, for example, a pattern of a one-dimensional structure or a pattern of a two-dimensional structure. Further, when ejecting the dispersion liquid to the upper part of the relief shape, the fine metal particles are arranged along the upper ridgelines of the projecting sections, and during the process of evaporating (drying or heated-air drying) to remove the dispersion medium, the fine metal particles can be arranged along the pattern of the relief structure thus formed.

Application Example 7

In the method of manufacturing a sensor chip of the above application example of the invention, it is preferable that the ejecting is performed using an inkjet process.

As an arrangement method of the fine metal particles of the related art, there has been known a method of dropping a droplet of the dispersion liquid on the substrate and then centrifugally spreading it in a thin and even manner using a device such as a spin coater. In such a method there is a problem that the fine metal particles having a specific gravity higher than that of the dispersion medium also centrifugally spread outward, and as a result, a large number of fine metal particles are wasted. In contrast, according to this application example of the invention, since it becomes possible to leave all of the fine metal particles included in the dispersion liquid on the relief structure using the inkjet process, it becomes possible to efficiently manufacture the sensor chip.

Application Example 8

In the method of manufacturing a sensor chip of the above application example of the invention, it is preferable that a size of spread after ejecting the dispersion liquid is smaller than a forming area of the relief structure.

The area located at roughly central portion of the substrate and provided with the relief structure corresponds to the sensor section, and the dispersion liquid including the fine metal particles is ejected on the roughly central portion of the sensor section as a droplet. Immediately after the ejection, the droplet is attached so as to rise with respect to the sensor section due to the surface tension. Subsequently, the dispersion medium is gradually dried while penetrating into the recessed sections of the relief structure. During this process, a large proportion of the fine metal particles dispersed therein is captured by the recessed sections in the relief structure. This is caused by the evaporation of the dispersion medium and the action of the dispersion medium percolating through the recessed sections of the relief structure to seep outside. As a result, most of the fine metal particles included in the dispersion liquid can be left in the relief structure, and thus the sensor chips can efficiently be manufactured without incurring waste.

Application Example 9

This application example of the invention is directed to a detection device including a suction section and a discharge section adapted to transport a gaseous detection target substance on a sensor chip, a section adapted to excite Raman scattering, an optical section adapted to remove Rayleigh scattered light, a spectroscopic section adapted to disperse the Raman scattered light, a light receiving section adapted to convert the light dispersed into an electric signal, and a signal processing/control section adapted to perform signal processing and control on Raman information converted into the electric signal, wherein the detection target substance is detected using localized surface plasmon resonance and surface enhanced Raman scattering occurring between fine metal particles on the sensor chip.

According to this application example of the invention, the fine metal particles having the size in the order of several nanometers are arranged on the sensor chip so as to be aligned with minute gaps, and it results that the localized surface plasmon resonance excited by irradiating the fine metal particles with the laser beam occurs more efficiently. As a result, the surface enhanced Raman scattering is performed, and thus, the detection device capable of detecting the substance with high sensitivity can be realized.

BRIEF DESCRIPTION OF THE DRAWINGS

The invention will be described with reference to the accompanying drawings, wherein like numbers reference like elements.

DESCRIPTION OF EXEMPLARY EMBODIMENTS

Some embodiments of the invention will hereinafter be explained with reference to the accompanying drawings.

It should be noted that the drawings referred to in the following explanation are schematic diagrams having contraction scales in the vertical and horizontal directions of each of the constituents or the parts different from the actual ones in order for making the constituents have recognizable sizes.

Sensor Chip/First Embodiment

Figure 1:
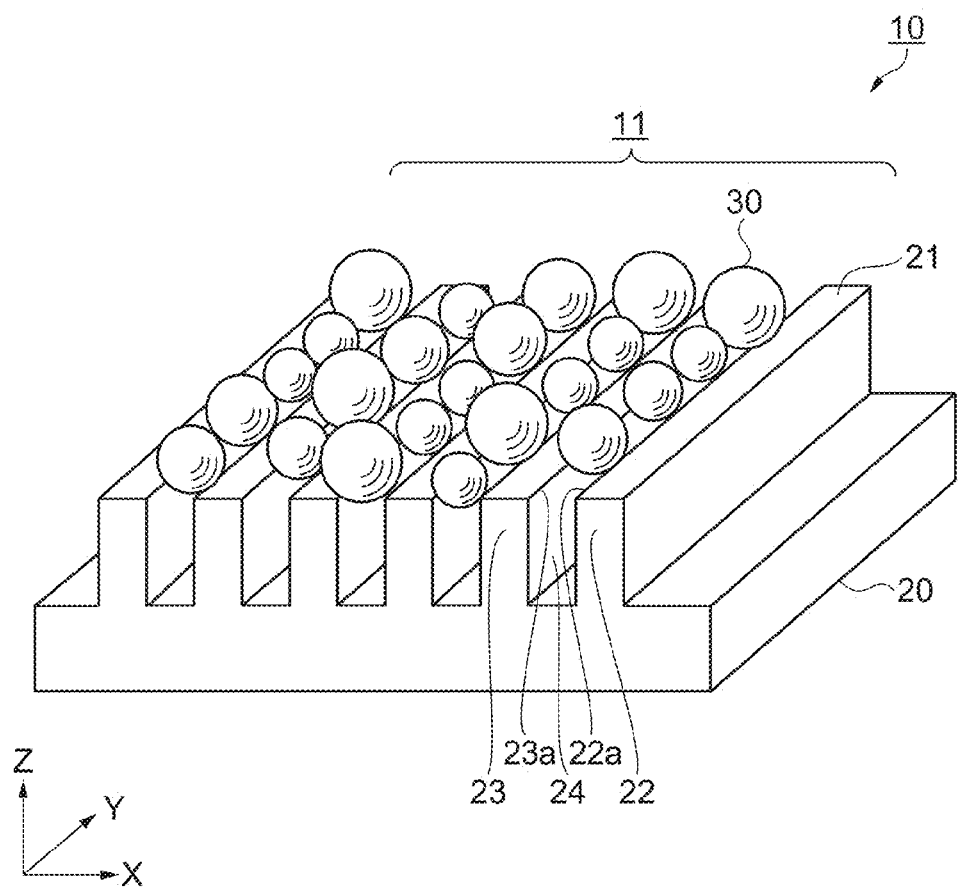
FIG. 1 is a perspective view showing a part of a sensor chip according to a first embodiment of the invention.
Figure 2:
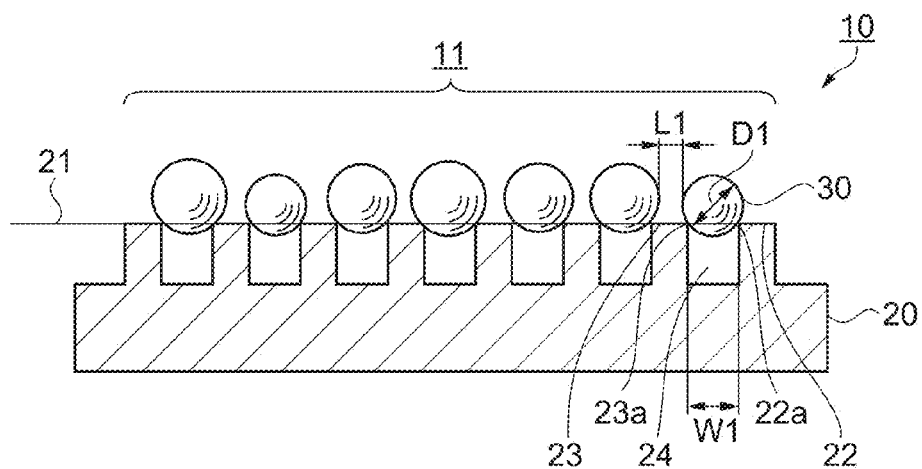
FIG. 2 is a cross-sectional view of the sensor chip according to the first embodiment.

FIG. 1 is a perspective view showing a part of a sensor chip according to a first embodiment of the invention, and FIG. 2 is a cross-sectional view of the sensor chip. In FIGS. 1 and 2, the sensor chip 10 is composed of a relief structure formed on a surface of a substrate 20, and an aggregate of a number of fine metal particles 30. The area composed of the relief structure and the fine metal particles is defined as a sensor section 11. The material of the substrate 20 is made of a dielectric substance, and quartz, quartz crystal, glass such as borosilicate glass, silicon, and so on are suitable therefor. In the case of setting the incident light to the substrate 20 side, the substrate which is transparent with respect to the incident light is suitable, and in the case of setting the incident light to the fine metal particle side, the transparent substrate is not necessarily required.

The relief structure is formed to have a linear grating shape, and is formed by forming protruding sections 22, 23, . . . , by digging down recessed sections 24 from the upper surface 21 of the substrate 20 using an etching process. In the example shown in FIG. 1, the protruding sections 22, 23, . . . , form a single-dimensional structure in which the protruding sections 22, 23, . . . , are each disposed linearly in the Y direction, arranged in the X direction in parallel to each other, and protrude so as to be roughly perpendicular to the upper surface of the substrate 20 (Z direction). It should be noted that the relief structure is not limited to the linear arrangement as shown in the drawing, but can also have a concentric circular shape or a spiral shape.

As the material of the fine metal particles, gold (Au), silver (Ag), copper (Cu), aluminum (Al), platinum (Pt), palladium (Pd), molybdenum (Mo), and chromium (Cr), and alloys and complexes of these metals are suitable. The average particle diameter of the fine metal particles 30 is preferably equal to or smaller than 200 nm with which gravitational sedimentation in the mixture with the dispersion medium described later is hard to occur and which is smaller than the wavelength of the incident light, and is more preferably in a range of 10 nm through 100 nm. In the present embodiment, there is used Au or Ag having a property of strongly developing surface plasmon resonance (SPR), localized surface plasmon resonance (LSPR), or surface-enhanced Raman scattering (SERS). It should be noted that the fine metal particles 30 are not required to have particle sizes equal to each other providing the particle sizes are in a range of 10 nm through 100 nm.

Further, the distance W1 (the width of the recessed section 24) between the protruding sections adjacent to each other in the relief structure is set to be smaller than the average particle size D1 of the fine metal particles 30. Therefore, there is adopted a structure in which most of the fine metal particles 30 are supported by upper ridgelines 22a, 23a of the respective protruding sections 22, 23 adjacent to each other instead of being disposed inside the recessed section 24.

Further, the fine metal particles 30 are arranged in the Y direction along the recessed sections as shown in FIG. 1. On this occasion, the average particle diameter D1 of the fine metal particles 30 and the distance W1 between the protruding sections are set so that the gap L1 between the fine metal particles 30 adjacent to each other in the X direction has a dimension suitable for forming an enhanced electric field due to the surface plasmon resonance.

Sensor Chip/Second Embodiment

Subsequently, a sensor chip according to a second embodiment of the invention will be explained with reference to the accompanying drawings. The second embodiment is characterized in that the relief structure is formed to have a grid shape having a two-dimensional structure.

Figure 3:
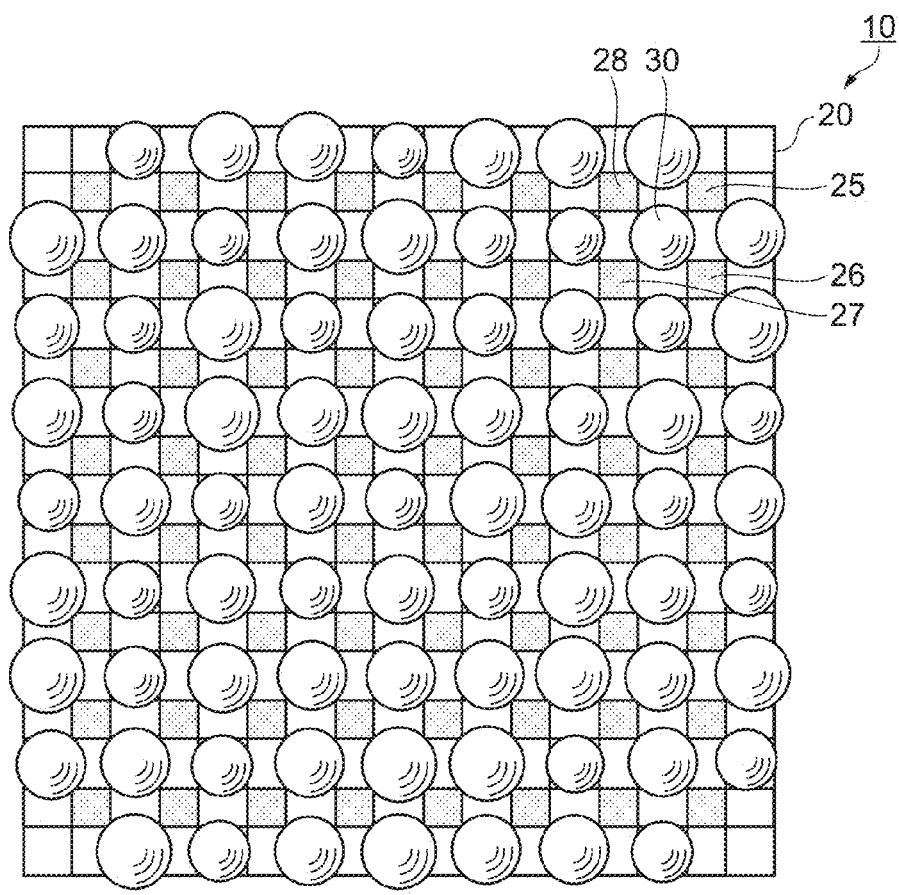
FIG. 3 is a plan view showing a part of a sensor chip according to a second embodiment of the invention.

FIG. 3 is a plan view showing a part of the sensor chip according to the second embodiment. It should be noted that the cross-sectional structure can be expressed similarly to FIG. 2, and is therefore omitted. In FIG. 3, the relief structure has the protruding sections and the recessed sections arranged in each of the vertical and horizontal directions. Here, in the explanation showing one of the fine metal particles as an example, the fine metal particles 30 is arranged to be supported by four apexes at which respective ridgelines of the columnar protruding sections 25, 26, 27, and 28 intersect each other. In other words, setting a combination of the four intersections of the ridgelines of the protruding sections 25, 26, 27, and 28, and the fine metal particle 30 supported by the four intersections as an unit, the units are arranged in the vertical and horizontal directions of the substrate 20. It should be noted that although the portions (white portions in the drawing) other than the protruding sections 25, 26, 27, and 28 are the recessed sections in the present embodiment, it is also possible to adopt the relief structure obtained by exchanging the protruding section and the recessed sections with each other. In such a configuration, the fine metal particles 30 are each supported by the ridgelines of the protruding sections 25, 26, 27, and 28. Further, the planar shape of each of the protruding sections can be a rectangle or a circle.

The average particle diameter D1 of the fine metal particles, the distance W1 between the protruding sections, and the distance L1 between the fine metal particles are set to have the same relationship as in the first embodiment described above.

Principle of Sensing

Then, the principle of sensing using one of the sensor chips described above will be explained with reference to the accompanying drawing.

Figure 4:
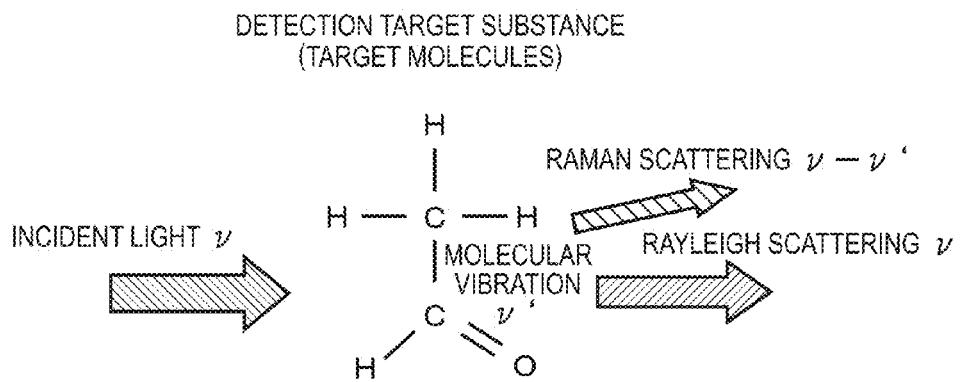
FIG. 4 is an explanatory diagram of Raman spectroscopy.
Figure 5:
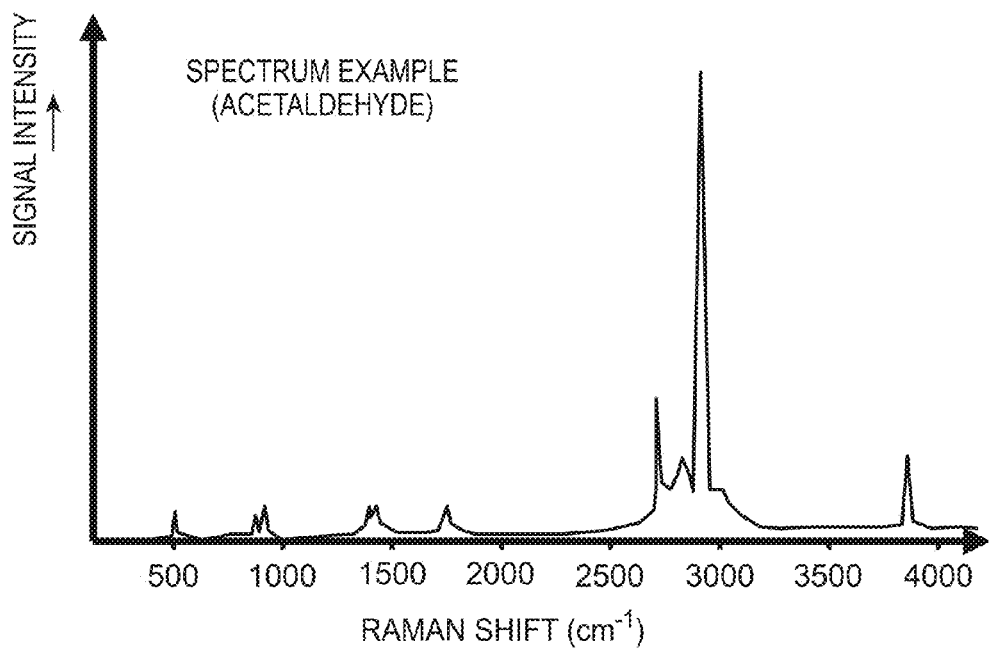
FIG. 5 is a spectrum chart showing a measurement example assuming that the detection target substance is acetaldehyde.
Figure 6:
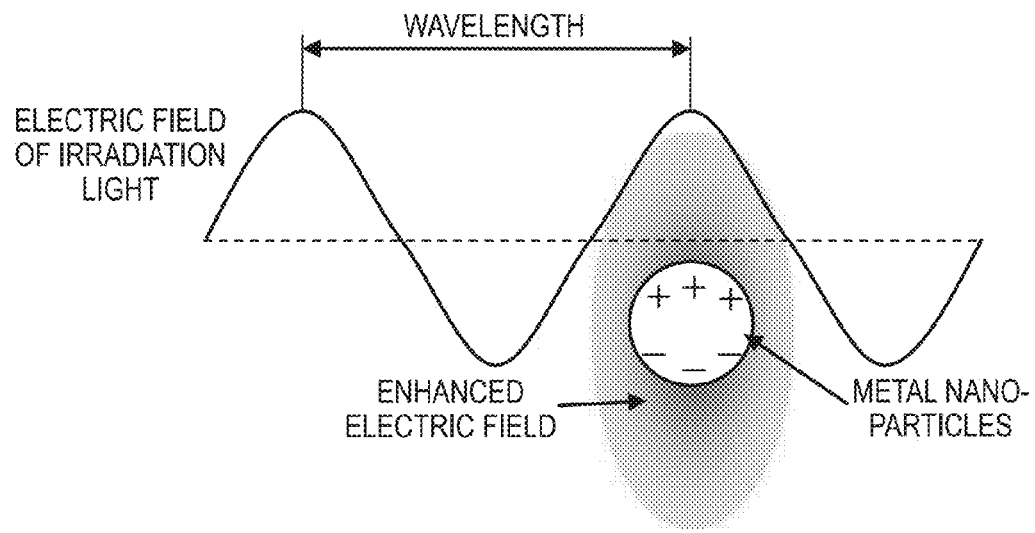
FIG. 6 is an explanatory diagram of an enhanced electric field formed when irradiating the fine metal particles with light.

FIG. 4 is an explanatory diagram of the Raman spectroscopy, FIG. 5 is a spectrum chart showing a measurement example assuming that the detection target substance is acetaldehyde, and FIG. 6 is an explanatory diagram of an enhanced electric field formed when irradiating the fine metal particles with light.

As shown in FIG. 4, when the target molecules as the detection target substance are irradiated with the incident light (with a wavelength ν), a most part thereof is scattered without being varied in the wavelength as the Rayleigh scattered light. A part thereof is scattered as the Raman scattered light (with a wavelength ν-ν') including information of the molecular vibration of the target molecules. It results that "fingerprint" spectrum of the target molecules (here the acetaldehyde molecules are shown as an example) shown in FIG. 5 can be obtained in the Raman scattered light.

FIG. 5 shows a measurement example of the spectrum when setting the detection target substance to acetaldehyde, with the lateral axis representing Raman shift (unit: $cm^{-1}$), and the vertical axis representing signal intensity. Due to the fingerprint spectrum, it is possible to identify the substance thus detected as the acetaldehyde molecules. However, the Raman scattered light (the Raman signal) is extremely faint, and therefore, it is difficult to detect the substance present in only minute amounts. Therefore, the surface plasmon resonance is used for generating the enhanced electric field to thereby enhance the Raman signal.

FIG. 6 is an explanatory diagram of an enhanced electric field formed when irradiating the fine metal particles with light. The surface plasmon resonance denotes the vibration mode of the electron wave causing the coupling with light under the boundary condition unique to the surface of the substance. Specifically, as shown in FIG. 6, when irradiating the fine metal particles smaller than the wavelength of the incident light with the light, the free electrons existing on the surface of each of the fine metal particles resonate due to the action caused by the electric field of the incident light. As a result of the condition in which the electric dipole due to the free electrons becomes in an aligned state, an enhanced electric field stronger than the electric field of the incident light is formed in the vicinity of the fine metal particles. This phenomenon is a phenomenon unique to the metal particles smaller than the wavelength of the light. Incidentally, the propagating surface plasmon exists on the metal surface on the one hand, the localized surface plasmon exists on the metal nano-particle on the other hand. when the localized surface plasmon, namely the surface plasmon localized on the microstructure of the surface, is excited, a remarkably enhanced electric field is induced. The phenomenon described above is called localized surface plasmon resonance.

In the embodiment described above, the fine metal particles are aligned on the substrate 20 to thereby be arranged so as to form the enhanced electric field in the gap between the fine metal particles. Here, if the target molecules as the detection target substance get into the structure, it results that the Raman scattered light is enhanced in the enhanced electric field, and thus a strong Raman signal can be obtained. Such Raman scattered light is referred to as surface enhanced Raman scattered light. As a result, the Raman spectroscopy can be performed even on the target molecules present in minute amounts. This is the principle of making it possible to detect minute amount of target molecules with high sensitivity.

The sensor chip 10 according to any one of the first and second embodiments described above is a sensor for detecting the detection target substance using the localized surface plasmon resonance and the surface enhanced Raman scattering. Therefore, according to the first and second embodiments, the fine metal particles 30 are arranged with the directions of the minute gaps formed between the fine metal particles aligned in accordance with the distance between the protruding sections 22, 23 (or the protruding sections 25, 26, 27, and 28) formed on the surface 20a of the substrate 20. Therefore, it results that the localized surface plasmon resonance occurs more efficiently. As a result, the surface enhanced Raman scattering for realizing the high sensitivity is performed, and thus, the sensor chip capable of detecting the substance with high sensitivity can be realized.

Further, the substrate 20 is made of a dielectric material. The sensor chip according to any of the embodiments described above is for enhancing the surface enhanced Raman scattering by the enhanced electric field due to the localized surface plasmon resonance occurring in the periphery thereof in the gap between the fine metal particles to thereby detect the fingerprint spectrum of the detection target substance. Therefore, by using a dielectric material as the material of the substrate 20, the influence of the medium in the periphery of the fine metal particles on the electric field can be eliminated to thereby prevent the peak intensity of the spectrum from being deteriorated.

Further, the average particle diameter D1 of the fine metal particles 30 is smaller than the wavelength of the incident light, and has a size suitable for forming the enhanced electric field due to the surface plasmon resonance. In the case of irradiating the fine metal particles smaller than the wavelength of the incident light with the light, it results that the free electrons existing on the surface of each of the fine metal particles are subjected to the action of the electric field of the incident light to thereby resonate. Thus, the condition in which the electric dipoles due to the free electrons are aligned is created in the periphery of each of the fine metal particles, and the enhanced electric field stronger than the electric field of the incident light can be formed.

Further, the distance W1 between the protruding sections adjacent to each other in the relief structure is smaller than the average particle size D1 of the fine metal particles 30. According to this configuration, the fine metal particles can be arranged with appropriate gaps by the upper ridgelines 22a, 23a of the protruding sections 22, 23 without dropping off in the recessed sections 24.

Further, the fine metal particles are each made of gold (Au), silver (Ag), copper (Cu), aluminum (Al), platinum (Pt), palladium (Pd), molybdenum (Mo), or chromium (Cr), or alloys or complexes of any of these metals. If those made of the material described above are used as the fine metal particles, it is possible to develop the surface plasmon resonance (SPR), the localized surface plasmon resonance (LSPR), and the surface enhanced Raman scattering (SERS), and in particular, Au or Ag can develop these phenomena strongly, and thus it becomes possible to detect the detection target substance with high sensitivity.

Sensor Chip/Third Embodiment

Subsequently, a sensor chip according to a third embodiment of the invention will be explained with reference to the accompanying drawings. The third embodiment is characterized by being different from the first and second embodiments in the cross-sectional shape of the relief structure. Therefore, the different point will be explained.

Figure 7:
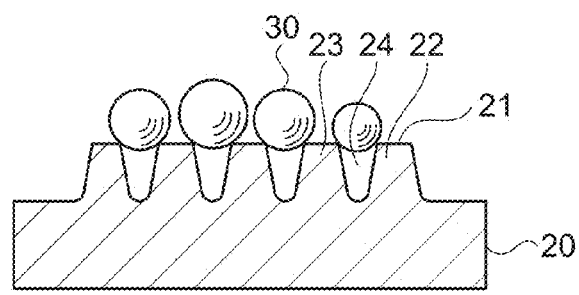
FIG. 7 is a cross-sectional view showing a part of a sensor chip according to a third embodiment of the invention.

FIG. 7 is a cross-sectional view showing a part of the sensor chip according to the third embodiment. In FIG. 7, the recessed sections of the relief structure are each formed having tilted walls (a tapered shape) with the bottom width narrower than the width on the upper surface 21 of the substrate 20. Such a shape can be applied to both of the one-dimensional structure of the first embodiment and the two-dimensional structure of the second embodiment described above (the case of the first embodiment is shown in the drawing).

The fine metal particles 30 are each held by the protruding sections 22, 23 to thereby form a predetermined arrangement structure.

Even by adopting such a configuration, advantages substantially the same as in the first and second embodiments can be obtained. Further, in the case of forming the recessed sections 24 using the etching process or the like, the recessed sections 24 each have the tapered shape in some cases. There is an advantage that the recessed sections 24 become easy to manufacture by setting the relationship between the distance W1 between the protruding sections adjacent to each other in the relief structure, the average particle diameter D1 of the fine metal particles 30, and the distance L1 between the fine metal particles similar to the cases of the first and second embodiments described above.

Sensor Chip/Modified Example

Subsequently, a sensor chip according to a modified example will be explained with reference to the accompanying drawings. The modified example is characterized in that the fine metal particles are arranged on the upper surface 21 of the substrate 20 using an inkjet process.

Figure 8:
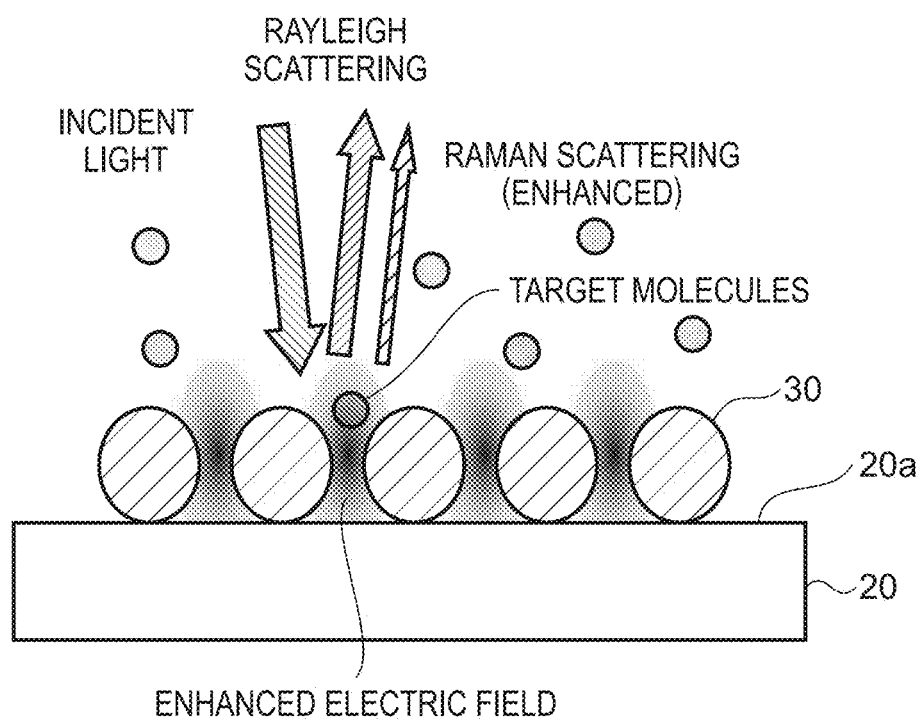
FIG. 8 is an explanatory diagram of an enhanced electric field formed when irradiating the metal nano-particles according to a modified example with light.

FIG. 8 is an explanatory diagram of an enhanced electric field formed when irradiating the fine metal particles according to the modified example with the light. The sensor chip 10 has the fine metal particles 30 arranged on the substrate surface 20a so as to form a single layer. The fine metal particles 30 can be adsorbed to the substrate 20 by dropping a dispersion liquid including the fine metal particles 30 mixed with the dispersion medium onto the substrate surface 20a using the inkjet process, and then evaporate the dispersion medium.

In such a configuration, as shown in FIG. 8, the fine metal particles 30 are formed on the substrate 20 in an arrangement capable of forming the enhanced electric field in the gaps therebetween in advance. Here, if the detection target substance (the target molecules) gets into the structure, it results that the Raman scattered light is enhanced in the enhanced electric field, and thus a strong Raman signal can be obtained. According to this structure, although the detection sensitivity is slightly degraded compared to the case of arranging the fine metal particles using the relief structure as in the first and second embodiments, it becomes possible to arrange the fine metal particles to have the distance L1 therebetween suitable for developing the localized surface plasmon resonance.

Method of Manufacturing Sensor Chip

Then, a method of manufacturing the sensor chip will be explained with reference to the accompanying drawings.

Figure 9A:
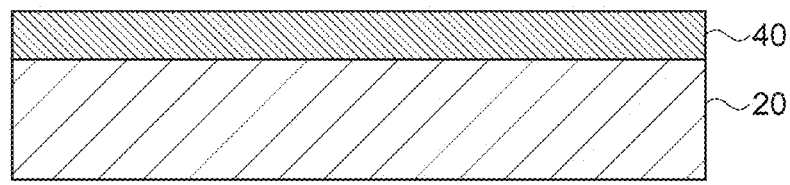
FIGS. 9A through 9D are cross-sectional diagrams showing a principal manufacturing process of the sensor chip.

FIGS. 9A through 9D, 10E, and 10F are cross-sectional diagrams showing a principal manufacturing process of the sensor chip. As the material of the substrate 20, there can be used quartz, quartz crystal, glass such as borosilicate glass, silicon, and so on. Here, the explanation will be presented showing a quartz plate as an example. Firstly, as shown in FIG. 9A, a resist 40 is applied to a surface of the clean substrate 20 with a device such as a spin coater, and is then dried. The laser interference exposure is performed thereon for forming a desired relief pattern.

In the present embodiment, since the dimensions of the fine metal particles and the relief structure are smaller than the wavelength (here, in a range from visible light to near infrared light) of the light to be applied, exposure devices using the electron beam exposure method, the optical interference exposure method with an ultraviolet laser, and so on can be used. The electron beam exposure method offers high flexibility of exposure, but has limitations in mass productivity on the negative side. Therefore, the optical interference exposure device using the ultraviolet laser superior in mass productivity is used here.

Figure 11:
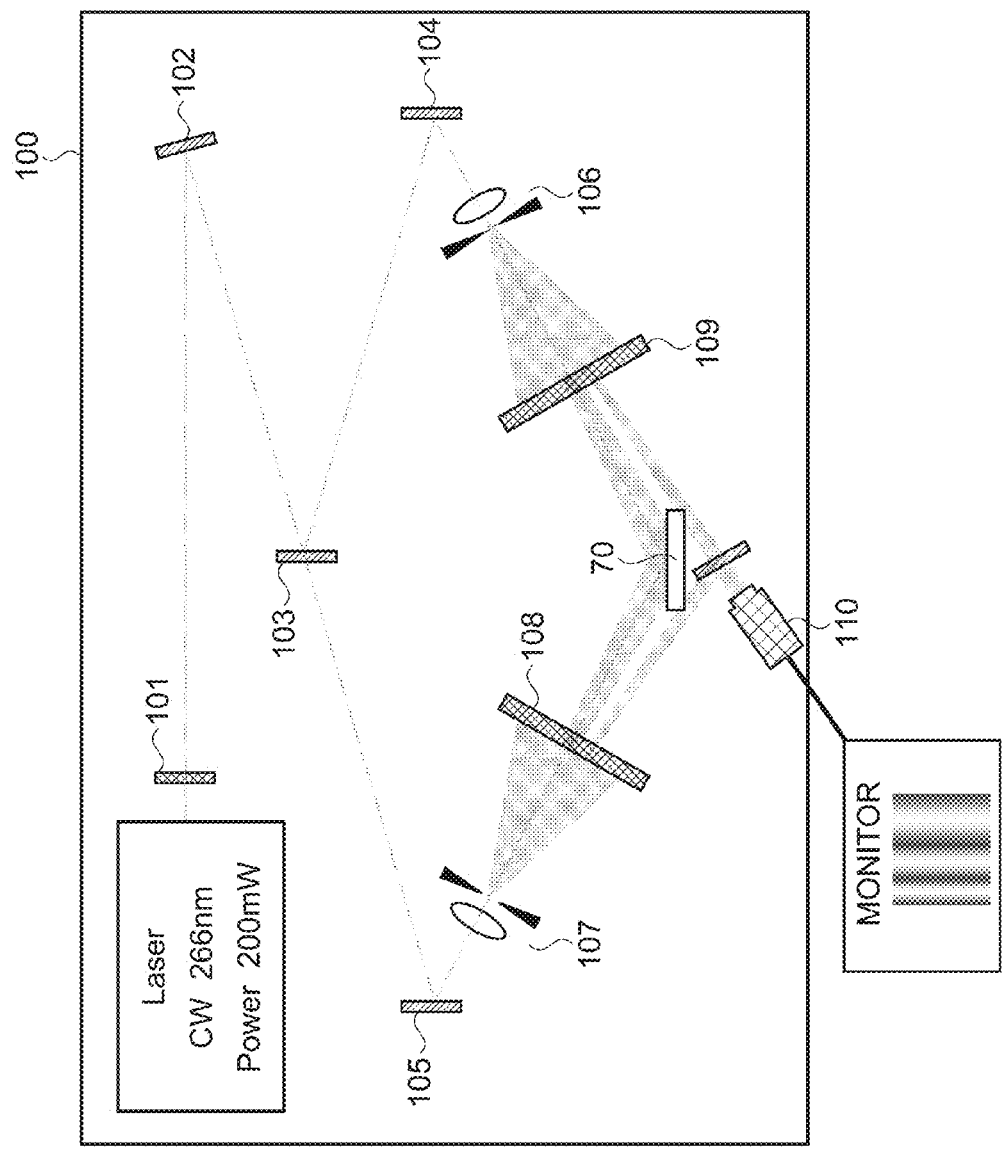
FIG. 11 is a system explanatory diagram showing a rough outline of an optical interference exposure device using an ultraviolet laser.

FIG. 11 is a system explanatory diagram showing a rough outline of the optical interference exposure device using the ultraviolet laser. The laser beam output from the laser device is folded by a mirror 102 after passing through a shutter 101, and is then branched into two directions by a half mirror 103. The ultraviolet laser beams thus branched are folded by mirrors 104, 105, and are then spread by passing through field lenses 106, 107 and pinholes, respectively. Subsequently, masks 108, 109 are irradiated with the respective ultraviolet laser beams thus spread to thereby form an interference pattern, and then the substrate 20 (a sensor substrate 70) coated with a resist 40 (see FIG. 9A) with the interference pattern. On this occasion, a variety of patterns of exposure become possible in accordance with the exposure configuration of the interference pattern.

Figure 9B:
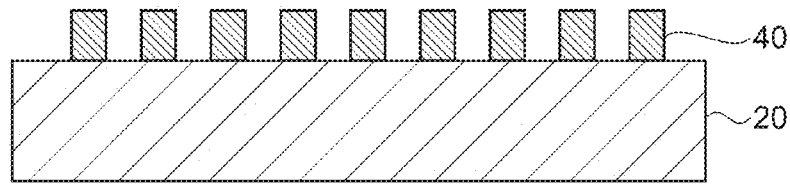

In the present embodiment, a continuous-wave YVO4 laser (wavelength of 266 nm, maximum power of 200 mW) is used as the light source of the interference exposure. A positive resist is used, and the film thickness of the resist is set to 1 μm. Regarding the exposure pattern of the resist, by forming one of the patterns to have a grating shape and forming the other of the patterns to have also a grating shape, a variety of patterns can be formed in accordance with the angle at which the both patterns intersect each other, and the size thereof can be made as small as a half of the laser wavelength. A latent image of the interference pattern of the both patterns is formed on the resist 40, and the resist is developed to thereby form a desired pattern (FIG. 9B).

Figure 9C:
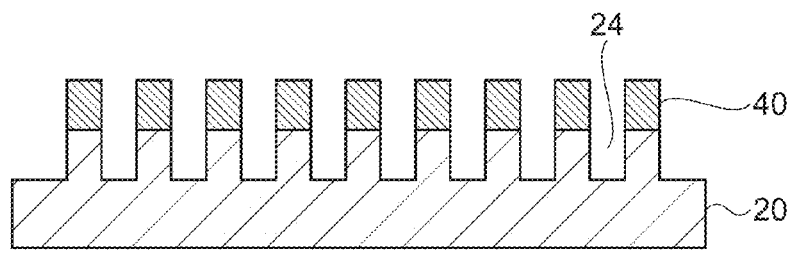
Figure 9D:
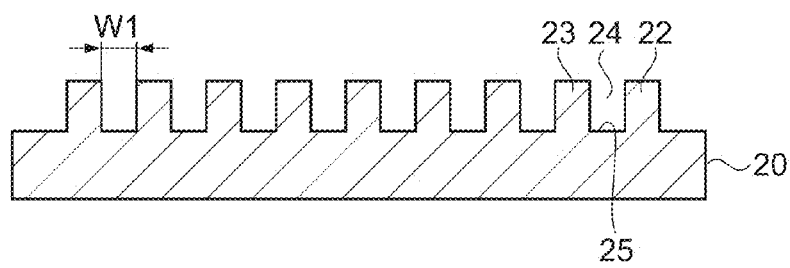

Subsequently, the portions not protected by the resist pattern are etched to thereby form the recessed sections 24 on the substrate 20 (FIG. 9C). Further, the resist 40 remaining on the substrate 20 is removed (FIG. 9D). In such a manner as described above, the relief structure composed of the protruding sections 22, 23, . . . , and the recessed sections 24 is formed. Here, the distance W1 (the width of the recessed section 24) between the protruding sections adjacent to each other is set to be smaller than the average particle size D1 of the fine metal particles 30.

Figure 10E:
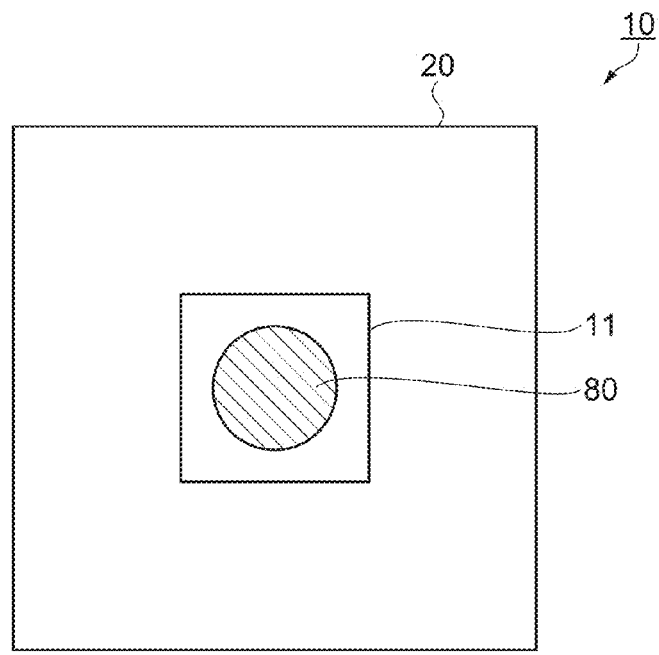
FIGS. 10E and 10F are cross-sectional diagrams showing the principal manufacturing process of the sensor chip.

Subsequently, the fine metal particles 30 are arranged on the relief structure using the inkjet process. As shown in FIG. 10E, the portion provided with the relief structure located at roughly central part of the substrate 20 corresponds to the sensor section 11, and the dispersion liquid 80 including the fine metal particles is ejected on the roughly central portion thereof using an inkjet device. It should be noted that the ejection is performed so that the size of the spread of the dispersion liquid after ejected on the relief structure becomes smaller than the forming area of the relief structure.

Immediately after the ejection, the dispersion liquid is landed on the sensor section 11 so as to rise therefrom due to the surface tension. Subsequently, the dispersion medium is gradually dried while penetrating into the recessed sections 24 of the relief structure, and is thus removed.

It should be noted that the dispersion medium can be removed by heated-air drying. In the evaporation process of the dispersion medium, most of the fine metal particles dispersed therein are captured by the recessed sections 24 with the upper ridgelines 22a, 23a of the protruding sections 22, 23 of the relief structure. The adsorption of the fine metal particles 30 to the relief structure is caused by the evaporation of the dispersion medium from the upper surface, and the action of the dispersion medium percolating through the recessed sections 24 of the relief structure to seep outside.

Then, an example of the method of manufacturing the fine metal particles will be explained. It should be noted that the drawing thereof will be omitted. Firstly, a rotatable vacuum chamber is made vacuum while circulating the liquid composed of alkyl naphthalene with low vapor pressure and polyamine as a lipophilic surfactant on the inside wall of the vacuum chamber. The degree of vacuum is about $10^2$ (Pa). The fine metal particles are evaporated from the evaporation source capable of evaporating the metal contained in a melting pot with a heater (a resistive heater or an inductive heater) existing therein, then captured by the liquid circulated on the inner wall of the vacuum chamber, and then accumulated in the lower part of the vacuum chamber with the rotation as a liquid. As the material of the fine metal particles, Au, Ag, Al, Cu, Pd, Cr, Pt, and so on are suitable. The particle diameter thereof is preferably equal to or smaller than 200 nm with which gravitational sedimentation is hard to occur and which is smaller than the wavelength of the incident light, and is more preferably in a range of 10 nm through 100 nm.

As a specific example, a method of manufacturing silver nano-particles having a property of strongly developing the SPR, LSPR, and SERS will be explained. As the silver nano-particles, it is preferable to use silver nano-particles having an average particle diameter of no larger than 100 nm generated by adding iron sulfate to a silver nitrate solution under existence of sodium citrate to thereby reduce the silver ions. It is preferable that iron sulfate and sodium citrate are mixed with each other in advance, and then the silver nitrate solution is poured in the mixed solution under the room temperature to thereby reduce the silver nitrate. The silver concentration in the silver nitrate solution is appropriately in a range of 1 g/L through 200 g/L, and the amount of iron sulfate is only required to be an amount with which the silver nitrate can sufficiently be reduced.

Further, the amount of sodium citrate is preferably in a range of 2 through 7 times of the number of moles of silver. The mixture of the silver nitrate solution and the iron sulfate solution is preferably performed by pouring the solution at 5 through 20 ml/min in every supply nozzle. After the mixture, the solutions are agitated to thereby be reacted each other evenly. Silver is reduced due to the reaction, and a silver colloidal solution including silver ultrafine particles (silver nano-particles) having a particle diameter of nanometer size can be obtained. By performing solid-liquid separation on the silver colloidal solution, and then cleansing the solid content thus separated with sodium citrate, a silver colloidal liquid having the silver nano-particles dispersed can be obtained.

The dispersion liquid of the silver nano-particles can be manufactured by, for example, dispersing material fine particles in an appropriate dispersion medium to thereby obtain the dispersion liquid, and then adding thiol compound into the dispersion liquid. The concentration of the fine metal particles to the dispersion medium is preferably in a range of 1 through 50% by weight, and is more preferably in a range of 4 through 20% by weight. If the percentage by weight of the fine metal particles is too low, the density of the fine metal particles formed becomes lower, and the enhanced electric field due to the localized surface plasmon resonance becomes weaker. If it is too high, in contrast, ejection of the droplets becomes unstable.

As the dispersion medium, there can be cited, for example, alcohols such as methanol, ethanol or isopropanol, butanol, octanol, ethylene glycol, diethylene glycol, or glycerine, Cellosolve™ such as methyl cellosolve, ethyl cellosolve, or phenyl cellosolve, esters such as methyl acetate, ethyl acetate, butyl acetate, or ethyl formate, ketones such as acetone, methyl ethyl ketone, diethyl ketone, methyl isobutyl ketone, methyl isopropyl ketone, or cyclohexanon, aliphatic hydrocarbons (paraffinic hydrocarbons) such as pentane, hexane, or octane, alicyclic hydrocarbons such as cyclohexane or methyl cyclohexane, aromatic hydro carbons such as benzene, toluene, xylene, benzenes having a long-chain alkyl group (alkyl benzene derivatives) such as hexylbenzene, butylbenzene, octylbenzene, nonylbenzene, decylbenzene, undecylbenzene, dodecylbenzene, tridecylbenzene, or tetradecylbenzene, halogenated hydrocarbons such as methylene chloride, chloroform, carbon tetrachloride, or 1,2-dichloroethane, aromatic heterocyclic compounds such as pyridine, pyrazine, furan, pyrrole, thiophene or methylpyrrolidone, nitriles such as acetonitrile, propionitrile, or acrylonitrile, amides such as N,N-dimethylformamide or N,N-dimethylacetamide, and these materials can be used alone or in combination. It should be noted that since the dispersion medium with high vapor pressure easily evaporates in the vicinity of the nozzle to easily cause clogging of the nozzle, it is required to take a device of, for example, covering the nozzle with a cap for preventing the evaporation except the period of ejecting the droplets.

As the method of dispersing the fine metal particles into the dispersion medium described above, there can be cited, for example, a method of dispersing them by mechanical impact or shear using a beads mill, a rocking mill, a homogenizer, and so on, and a method of dispersing them by a cavitation force of an ultrasonic wave, a high-pressure homogenizer, and so on. Among these methods, the dispersion method using an ultrasonic device, in particular, an ultrasonic homogenizer is frequently used. In the case of applying the ultrasonic wave to thereby perform the dispersion, as the frequency range, a range of 2 through 100 kHz is preferable, a range of 2 through 50 kHz is more preferable, and a range of 10 through 40 kHz is particularly preferable. Although the irradiation of the ultrasonic wave can be performed continuously or intermittently, if the irradiation time is long, the intermittent irradiation is more preferable. This is because there is concern that the heating due to the continuous irradiation of the ultrasonic wave for a long time exerts a harmful influence on the dispersion of the particles.

As the inkjet method, there are proposed a variety of types of methods. Broadly, they are classified into an electrostatic method, a piezoelectric method, and a film boiling inkjet method. The principle of the electrostatic method is that when a drive signal is provided to an electrostatic gap as an actuator, a diaphragm in a cavity is displaced to cause pressure variation in the cavity, and an ink droplet is ejected from the nozzle due to the pressure variation. The principle of the piezoelectric method is that when a drive signal is provided to a piezoelectric element as an actuator, a diaphragm in a cavity is displaced to cause pressure variation in the cavity, and an ink droplet is ejected from the nozzle due to the pressure variation. In contrast, the principle of the film boiling inkjet method is that a microscopic heater is provided inside the cavity, and is instantaneously heated to 300° C. or higher to thereby make the ink become in the film boiling state to generate a bubble, thus causing the pressure variation which makes the ink droplet be ejected from the nozzle. In the embodiment of the invention, either type of inkjet device can be used.

It should be noted that in the present embodiment the sensor chip 10 is manufactured using a batch process in which a number of sensor chips are arranged on a large-sized sensor substrate.

Figure 12:
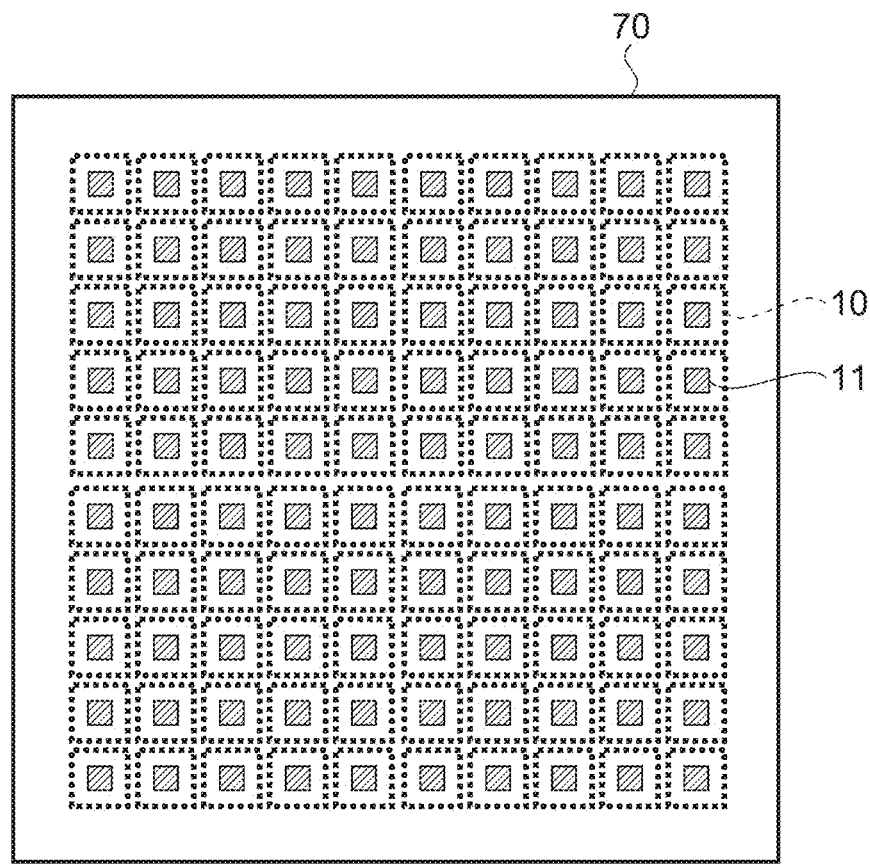
FIG. 12 is a layout diagram showing a layout configuration of the sensor chip on a sensor substrate.

FIG. 12 is a layout diagram showing a layout configuration of the sensor chip on the sensor substrate. A number of relief structures are formed on the sensor substrate 70 using the method (see FIGS. 9A through 9D, 10E, and 10F) described above. Each aggregate of these relief structures corresponds to the sensor section 11. After forming the relief structures, the dispersion liquid having the fine metal particles dispersed therein is ejected on each of the relief structures using the inkjet device to thereby form the sensor chips 10.

The sensor substrate 70 is fixed to an X-Y stage of the inkjet device, and a number of sensor chips 10 are arranged on the sensor substrate 70 as shown in FIG. 12. The X-Y stage is moved to a position where the dispersion liquid is ejected on the central portion of one of the sensor chips 10 one-by-one, and is then stopped once for positioning, and then the dispersion liquid is ejected from the nozzle selected. Subsequently, the X-Y stage is moved to the position corresponding to the central portion of the next one of the sensor chips 10, and then the dispersion liquid is ejected in a similar manner. By repeating the operation described above, the dispersion liquid is ejected on all of the sensor chips (the sensor sections 11). Subsequently, the dispersion medium is dried to thereby arrange the fine metal particles in each of the relief structures.

After forming the sensor chips 10 on the sensor substrate 70, the sensor substrate 70 is cut into individual sensor chips 10 using a dicing apparatus or the like, and thus the sensor chip 10 shown in FIGS. 1 and 2 is formed.

Therefore, according to the manufacturing method of the present embodiment, the relief structure is formed using the laser interference exposure process and the etching process. The arrangement of the relief pattern can be formed as, for example, a pattern of a one-dimensional structure or a pattern of a two-dimensional structure using such processes. Further, when ejecting the dispersion liquid to the upper part of the relief structure, the fine metal particles 30 are arranged along the upper ridgelines of each of the projecting sections, and during the process of drying (or heated-air drying) to remove the dispersion medium, the fine metal particles are arranged along the pattern of the relief structure thus formed.

Figure 15:
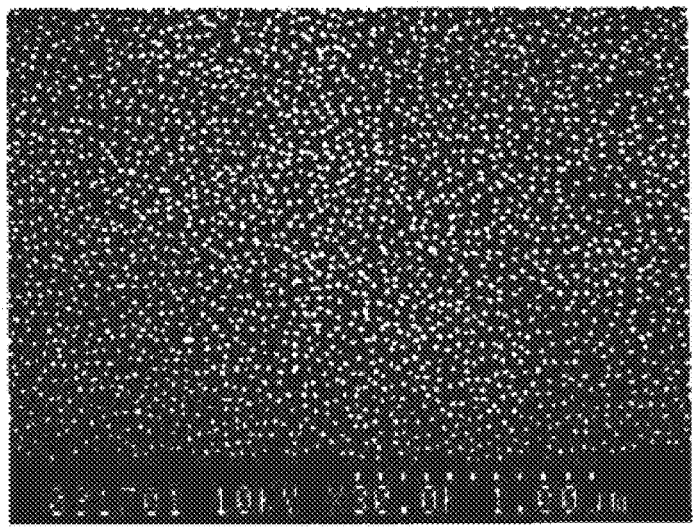
FIG. 15 is a diagram showing a state of fine metal particles disposed on a sensor chip using the related art technology.

In the present embodiment, the process of ejecting the dispersion liquid having the fine metal particles 30 dispersed in the dispersion medium on the upper part of the relief structure is performed using the inkjet device. As an arrangement method of the fine metal particles of the related art, there has been known a method of dropping a droplet of the dispersion liquid on the substrate and then centrifugally spreading it in a thin and even manner using a device such as a spin coater. Here, a state of fine metal particles disposed on a sensor chip using the related art technology is shown in FIG. 15. In this method there is a problem that the fine metal particles having a specific gravity higher than that of the dispersion medium also centrifugally spread outward, and as a result, a large number of fine metal particles are wasted. In contrast, according to the present embodiment, since it becomes possible to leave all of the fine metal particles included in the dispersion liquid on the relief structure using the inkjet process, it becomes possible to efficiently manufacture the sensor chip.

Figure 10F:
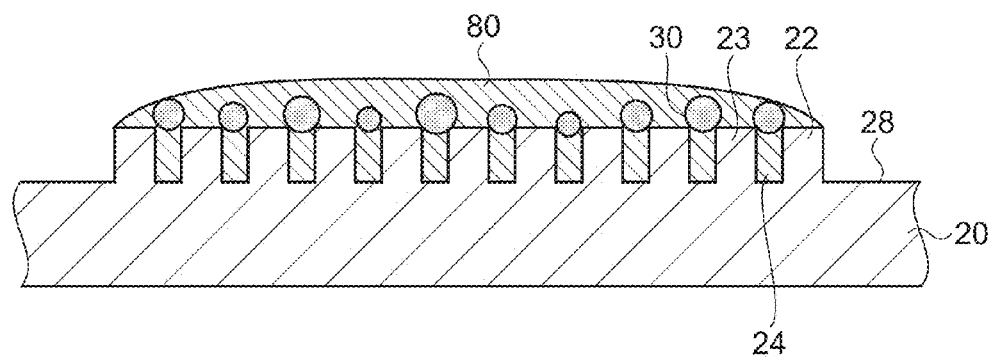

Further, as shown in FIGS. 10E and 10F, the size of the spread after ejecting the dispersion liquid 80 is set to be smaller than the forming area of the relief structure. Immediately after the ejection, the dispersion liquid is attached so as to rise with respect to the sensor section due to the surface tension. Subsequently, the dispersion medium is gradually dried while penetrating into the recessed sections of the relief structure. During this process, a large proportion of the fine metal particles dispersed therein is captured by the recessed sections in the relief structure. This is caused by the evaporation of the dispersion medium and the action of the dispersion medium percolating through the recessed sections of the relief structure to seep outside. As a result, most of the fine metal particles included in the dispersion liquid can be left in the relief structure, and thus the sensor chips can efficiently be manufactured without incurring waste.

Detection Device

Subsequently, a detection device will be explained with reference to the accompanying drawings.

Figure 13:
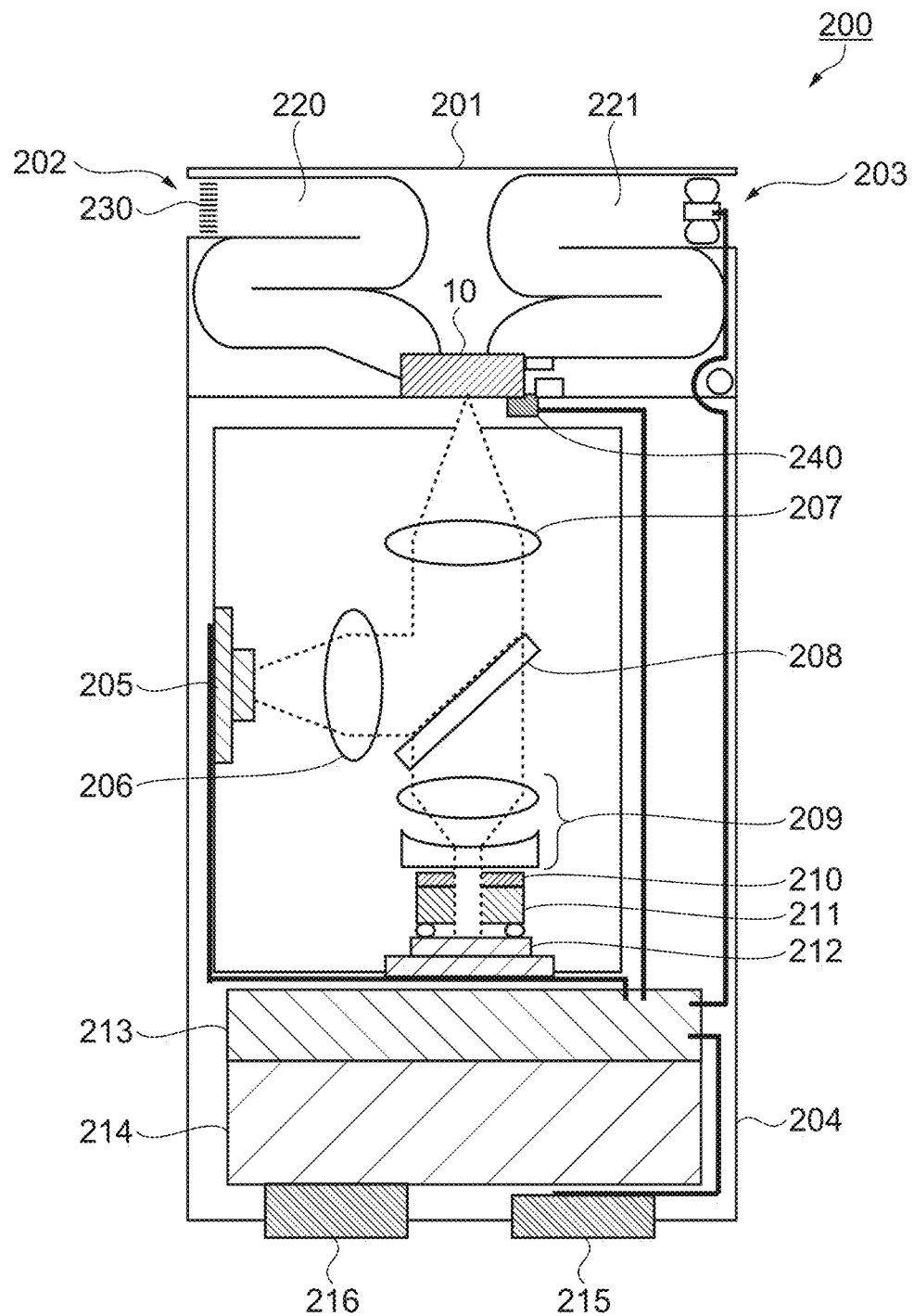
FIG. 13 is a configuration diagram showing an example of a configuration of a detection device.

FIG. 13 is a configuration diagram showing an example of a configuration of the detection device. The detection device 200 is composed of consumables such as the sensor chip 10 and a suction channel 220 replaced in each detection, and a main body section which can be used repeatedly.

The main body section is mainly composed of a sensor section cover 201 which can be opened and closed so as to store and replace the consumables, a discharge section 203, a housing 204 of the main body, a detection section including a light source 205, lenses 206, 207, and 209, a filter 210, a spectroscope 211, a light receiving element 212, and so on, a signal processing/control section 213 for processing the signal thus detected and controlling the detection section, a power supply section 214 for supplying the power, a connection sections 215, 216 for establishing the interface with the outside, and so on.

When making the discharge section 203 operate, negative pressure is applied to the suction channel 220, the channel inside the sensor chip 10, and a discharge channel 221, and a gaseous sample including the detection target substance (the target substance) to be detected is sucked in from a suction port 202. A dust filter 230 is located at the entrance of the suction channel 220, and relatively large powder dust, a part of moisture vapor, and so on are removed. The gaseous sample passes through the suction channel 220, and is then discharged from the discharge channel 221 via the channel inside the sensor chip 10. On this occasion, the target substance passes by the vicinity of the surface of the sensor chip 10, and is adsorbed or scattered by the sensor chip 10 to thereby become in the detectable state.

The shape of the channel for sucking in and discharging the gaseous sample is considered so that the external light can be prevented from entering the sensor section and that the fluid resistance to the gaseous sample decreases. By preventing the external light from entering the sensor section, the light other than the Raman scattered light, which becomes noise, is not input, and the S/N ratio of the signal is improved. It becomes necessary to select the material, color, and surface shape of the material forming the channel so as to be difficult to reflect the light in addition to the shape of the channel.

Further, by arranging that the fluid resistance to the gaseous sample decreases, a large amount of gaseous sample in the vicinity of the detection device 200 can be collected, and the detection with high sensitivity becomes possible. By forming these channels so as to have a smooth shape by eliminating the apexes as much as possible, accumulation of the gaseous sample can be eliminated. Further, as the discharge section 203, it is also necessary to select a fan motor or a pump having static pressure and air volume corresponding to the channel resistance.

The sensor chip 10 is irradiated with the light from the light source (the laser source) 205 of a linearly polarized light with a single wavelength, then the surface enhanced Raman scattered (SERS) light is radiated from the sensor chip 10, then collected by the lens 207, and then enters the light receiving element 212 with a half mirror 208. Since the light includes the Rayleigh beam having a wavelength equal to the wavelength of the incident light from the light source, the SERS light, and so on, the Rayleigh beam is removed by the filter 210, and then the light enters the spectroscope 211. The fingerprint spectrum unique to the target substance can be obtained by the spectroscope 211 and the light receiving element 212, and by matching the spectrum with the data held therein in advance, the target substance can be identified.

Once the detection of the target substance is terminated, the target substance is naturally diffused and discharged. The process of actively promoting the discharge using the discharge section 203 and then replacing the sensor chip 10 and so on having been used in preparation for the subsequent detection is performed in preparation for the subsequent detection. Here, the method of replacing the sensor chip 10 will be explained. In order to replace the sensor chip 10, the sensor section cover 201 is opened, and then the consumables integrally including the sensor chip 10, the suction channel 220, the dust filter 230, and so on are taken out. When new consumables is set there along a positioning member of a part of the sensor chip 10 after releasing the sealing section of the suction port of the consumables, a sensor chip detector 240 operates, and it is determined that the detection device 200 is in the state in which the detection device 200 can perform the detection.

Further, as the power supply section, a primary cell or a secondary cell can be used. In the case of the primary cell, an opening section (not shown) for replacing the battery is disposed in the lower part of the housing 204 of the main body, and if battery run out is displayed on the main body display (not shown), the battery can be replaced. In the case of the secondary battery, a connection section 215 is located on the lower part of the housing 204 of the main body, and if the buttery run out is displayed on the main body display, a battery charger is connected to the connection section 215 to thereby charge the secondary battery, and if completion of charge is displayed, the detection device 200 can be used again after removing the battery charger.

Then, a configuration and an operation of a control system of the detection device 200 will be explained with reference to the block diagram.

Figure 14:
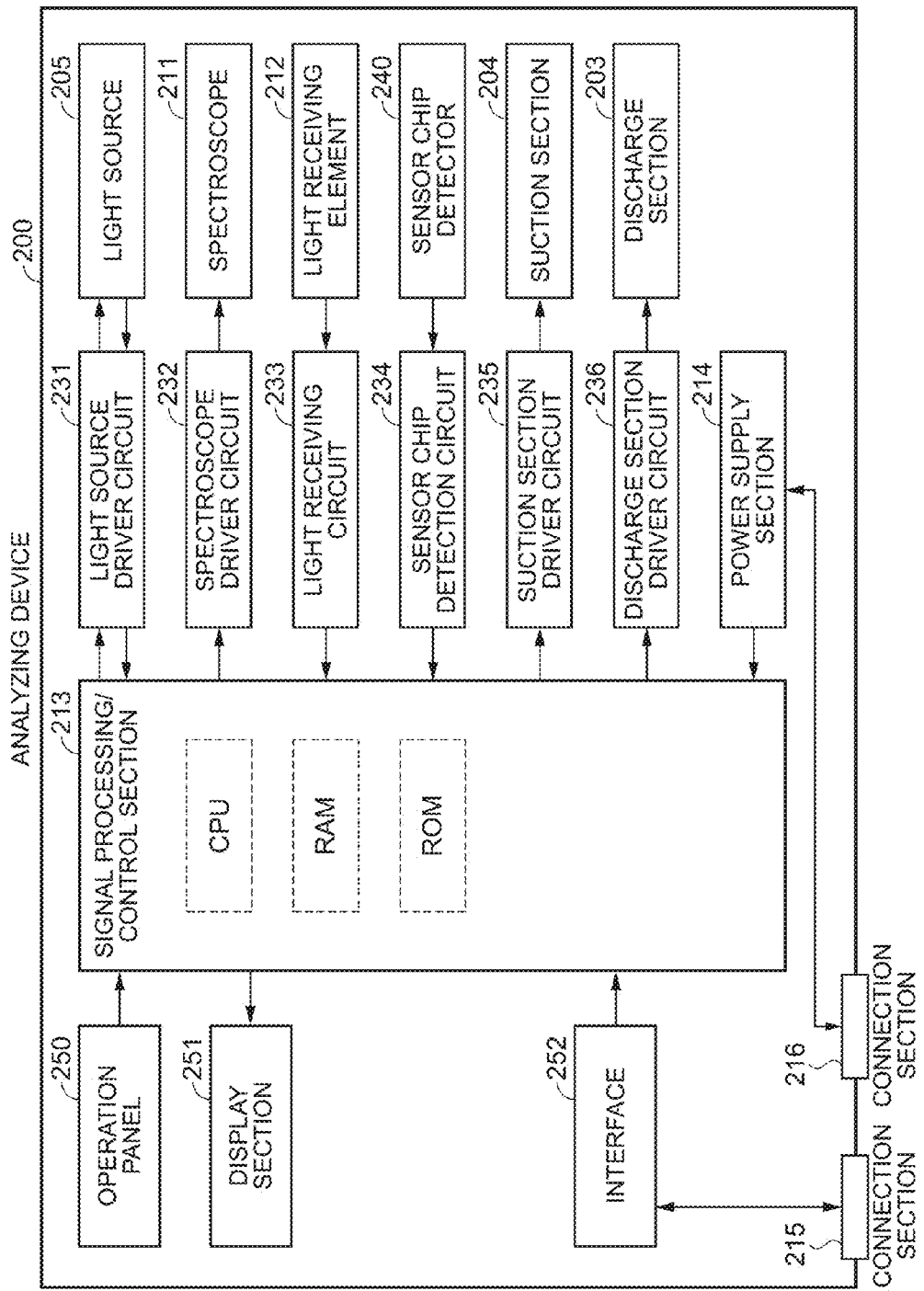
FIG. 14 is a block diagram showing a configuration of a control system of the detection device.

FIG. 14 is a block diagram showing the configuration of the control system of the detection device. It should be noted that FIG. 13 is also referred to. On the surface of the detection device 200, there are provided an operation panel 250, a display section 251, the connection section 215 for the interface with the outside, and the power supply section 214. In the case in which the power supply section 214 is a secondary cell, the connection section 216 for the battery charge is also provided. In the inside of the sensor section cover 201 in the upper part of the main body, there are disposed the sensor chip 10, and the sensor chip detector 240 for detecting presence or absence of the sensor chip 10, and reading the code of the sensor chip 10, and the information thereof is transmitted to a central processing unit (CPU) constituting the signal processing/control section 213 via a sensor chip detection circuit 234, and the determination is performed. Since this state is a state in which the preparation for detection is completed, the display signal representing the ready state is output from the CPU to the display section 251. The operator looking at the display outputs the instruction signal representing start of detection from the operation panel 250 to the CPU.

When the CPU receives the signal representing start of detection, the CPU firstly outputs the signal for operating the light source to a light source driver circuit 231 to thereby operate the light source 205. The light source 205 incorporates a temperature sensor and a light intensity sensor, and the information thereof is transmitted to the CPU, and then the CPU determines whether or not the operation is in a stable state. If the determination is positive, then the instruction signal of making the discharge section 203 operate is transmitted from the CPU to a suction section driver circuit 235 in order to guide the gaseous sample including the target substance to be detected to the vicinity of the surface of the sensor chip 10, and the gaseous sample enters the suction port 202, passes through the suction channel 220, the sensor chip space, and the discharge channel 221, and is then discharged to the outside.

Regarding the operation of the detection system, there exists the light source 205 (the laser source) for radiating the stable linearly polarized light with a single wavelength, and the light source 205 is driven by the light source driver circuit 231 in accordance with the signal from the CPU, and radiates the laser beam. The sensor chip 10 is irradiated with the laser beam, and thus the Rayleigh beam and the surface enhanced Raman scattered (SERS) light enter the light receiving side via the lenses 206, 207, and the half mirror 208.

Firstly, bypassing through the filter 210 for blocking the Rayleigh beam, the SERS light alone enters the spectroscope 211. The spectroscope 211 is controlled by a spectroscope driver circuit 232. In the case of adopting an etalon using the Fabry-Perot resonance, the band ($\lambda 1$ through $\lambda 2$) and the half bandwidth of the light transmitted therethrough are set, and the intensity of the optical signal corresponding to the half bandwidth is repeatedly detected by the light receiving element 212 while changing the wavelength of the light transmitted therethrough from X1 to X2 by the half bandwidth, and then the intensity of the optical signal is converted into an electrical signal by a light receiving circuit 233. According to such an operation as described above, it results that the spectrum of the SERS light thus detected can be obtained.

The spectrum of the SERS light of the target substance thus obtained is compared with the spectrum data stored in the ROM of the signal processing/control section 213 to thereby making a judgment on whether or not the target substance is the objective substance, and thus the identification of the substance is performed. In order to notify the operator of the judgment result, the result information is transmitted from the CPU to the display section 251, and is then displayed. In the case of transmitting the substance identification result to the outside as information, it is arranged to transmit the information from the connection section 215 based on an interface standard determined in advance.

As the power supply section 214, a primary cell, a secondary cell, and so on can be used. In the case of the primary cell, the CPU compares the information stored in the ROM and the voltage information of the primary cell thus obtained with each other to determine whether or not the voltage of the primary cell becomes lower than a predetermined voltage, and if it is lower than the predetermined voltage, the display for the battery replacement is displayed on the display section 251. It is therefore possible for the operator to replace the primary cell and then use the detection device again with reference to the display.

In the case of the secondary cell, the CPU compares the information stored in the ROM and the voltage information of the secondary cell thus obtained with each other to determine whether or not the voltage of the secondary cell becomes lower than a predetermined voltage, and if it is lower than the predetermined voltage, the display representing that the battery charge is necessary is displayed on the display section 251. With reference to the display, the operator connects the battery charger to the connection section 216 and performs the battery charge until the predetermined voltage is reached, and thus the detection device can be used repeatedly.

In the detection device 200, the fine metal particles having the size in the order of several nanometers are arranged on the sensor chip 10 so as to be aligned in the direction of the minute gaps, and it results that the localized surface plasmon resonance excited by irradiating the fine metal particles with the laser beam occurs more efficiently. As a result, the surface enhanced Raman scattering is performed, and thus, the detection device capable of detecting the substance with high sensitivity can be realized.

According to the sensor chip 10 and the detection device 200 explained hereinabove, detection of a variety of detection target substances can be performed. The detection target substances will hereinafter be cited as an example.

In the security field, detection of narcotic drugs and explosives performed in airports, seaports, and transportation facilities, and detection of combustible hazardous materials are possible.

In the medical/healthcare field, it is possible to detect a variety of types of viruses as causes of infectious diseases typified by flu, to determine presence or absence of periodontal disease by detecting hydrogen sulfide, methyl mercaptan, and dimethyl sulfide included in an oral gas, and to perform an inspection of asthma by detecting nitric monoxide (NO) included in an exhaled gas. Further, it is also possible to perform a screening test on cancer by detecting volatile organic compound (VOC) included in an exhaled gas, to perform fat-burning monitor by detecting acetone included in an exhaled gas, and to perform cholesterol monitor by detecting isoprene included in an exhaled gas, for example.

Further, it is possible to detect benzene, toluene, xylene, ethyl benzene, styrene, formaldehyde, and so on as the volatile organic compound (VOC) included in air in the room.

The entire disclosure of Japanese Patent Application No: 2010-287189, filed Dec. 24, 2010 are expressly incorporated by reference herein.

What is claimed is:

1. A sensor chip comprising:
a substrate;
a relief structure arranged on an uneven surface of the substrate, the relief structure having a recessed section, protruding sections located on both sides of the recessed section, the protruding sections having upper ridgelines; and
a plurality of fine metal particles that each have a spherical shape, each of the plurality of fine metal articles abutting two adjacent upper ridgelines, wherein
the plurality of fine metal particles are spaced apart from one another so that a gap is formed between at least a part of the plurality of fine metal particles,
the recessed section in the relief structure is configured with a plurality of groove elements in a plan view.

2. The sensor chip according to claim 1, wherein
the gap is a minute gap causing surface plasmon resonance, and
the substrate is made of a dielectric material.

3. The sensor chip according to claim 1, wherein
an average particle diameter of the fine metal particles is smaller than a wavelength of an incident light, and has a size with which an enhanced electric field due to surface plasmon resonance is formed.

4. The sensor chip according to claim 1, wherein
a distance between the protruding sections located on the both sides of the recessed section in the relief structure is smaller than an average particle diameter of the fine metal particles.

5. The sensor chip according to claim 1, wherein
the fine metal particles are each made of one of gold (Au), silver (Ag), copper (Cu), aluminum (Al), platinum (Pt), palladium (Pd), molybdenum (Mo), and chromium (Cr), and alloys and complexes of any of these metals.

6. A detection device comprising:
a discharge member configured to create negative pressure inside of a passage in which a gaseous detection target substance flows; and
a sensor chip on which the gaseous detection target substance being supplied, the sensor chip includes:
a substrate;
a relief structure arranged on an uneven surface of the substrate, the relief structure having a recessed section, protruding sections located on both sides of the recessed section, the protruding sections having upper ridgelines; and
a plurality of fine metal particles that each have a spherical shape, each of the plurality of fine metal particles abutting two adjacent upper ridgelines, wherein
the plurality of fine metal particles are spaced apart from one another so that a gap is formed between at least a part of the plurality of fine metal particles;
a section adapted to excite Raman scattering;
an optical section adapted to remove Rayleigh scattered light;
a spectroscopic section adapted to disperse the Raman scattered light;
a light receiving section adapted to convert the light dispersed into an electric signal; and
a signal processing/control section adapted to perform signal processing and control on Raman information converted into the electric signal,
wherein the recessed section in the relief structure is configured with a plurality of groove elements in a plan view, and
wherein the detection target substance is detected using localized surface plasmon resonance and surface enhanced Raman scattering occurring between fine metal particles on the sensor chip.

* * * * *